United States Patent [19]

Bewick et al.

[11] Patent Number: 4,915,726
[45] Date of Patent: Apr. 10, 1990

[54] BIOLOGICAL CONTROL OF DODDER

[75] Inventors: Thomas A. Bewick; Jana S. Stewart; Larry K. Binning; Walter R. Stevenson, all of Madison, Wis.

[73] Assignee: Wisconsin Alumni Research Foundation, Madison, Wis.

[21] Appl. No.: 10,208

[22] Filed: Feb. 3, 1987

[51] Int. Cl.$^4$ .............................................. A01N 63/00
[52] U.S. Cl. ......................................... 71/79; 435/929
[58] Field of Search ...................... 71/79; 435/929, 911

[56] References Cited

U.S. PATENT DOCUMENTS 4,419,120 12/1983 Walker .................................... 71/79

OTHER PUBLICATIONS

Weidemann et al., "Control of Texas Gourd, *Cucurbita texana*, with Fusarium Solani" 2/88 U.S. Dept. of Agric. pp. 271-274.
Khodayari et al., "Applicators for a Weed Pathogen plus Acifluorfen in Soybean", 10/86, U.S. Dept Agric. pp. 37-40.
Bruckart, Weed Technology vol. 2 Ins. 3, 1988, "Bentazon Reduces Rust-Induced Disease in Yellow Nutsedge", pp. 299-303.
General Subject Index, Chem. Abstracts, 6615GS; (1972-1976) Fusarium tricinctum.
Ashton, F. M. and D. Santana, 1976, Cuscuta spp. (Dodder), A Literature Review of its Biology and Control, Univ. California Coop. Ext. Bull, 1880, 22 pp.
Dawson, J. H., F. M. Ashton, W. V. Welker, J. R. Frank, and G. A. Buchanan, 1984, Dodder and its Control, U.S.D.A. Farmers' Bull, No. 2276, 24 pp.
Rudakov, O. L, 1963, First Results in the Biological Control of Cuscuta spp., Zashchita Rastenii ot Vreditellwi Boleznei, Moscow, 8:25-26 (with translation).
Templeton, G. E., D. O. TeBeest, and R. J. Smith, 1979, Biological Weed Control with Mycoherbicides, Ann. Rev. Phytopathol., 17:301-310.
Walker, H. L., 1980, *Alternaria macrospora* as a Potential Biocontrol Agent for Spurred Anoda: Production of Spores for Field Inoculum, U.S. Dept. Agric., Sci. Ed. Admin., AAT-S-12, 5 pp.

*Primary Examiner*—Richard L. Raymond
*Assistant Examiner*—Raymond Covington
*Attorney, Agent, or Firm*—Lathrop & Clark

[57] ABSTRACT

A mycoherbicidal inoculum is disclosed for controlling the growth of dodder (Cuscuta spp.) on field crops. The inoculum is obtained from spores of *Fusarium tricinctum*, a species of Alternaria, and their mutations.

9 Claims, No Drawings

BIOLOGICAL CONTROL OF DODDER

FIELD OF THE INVENTION

The present invention relates in general to an inoculum for agricultural crops, and in particular to a mycoherbicide for controlling the growth of dodder (Cuscuta spp.) on field crops.

DESCRIPTION OF PRIOR ART

Farm crops are continually plagued by a variety of weeds which can stunt or damage crop growth or even completely destroy the crop. Most of the typical weeds grow in similar fashion to the crop itself in that they germinate and grow from the soil thus sapping many of the necessary nutrients and water from the soil.

Unlike the weeds described above, dodder is a parasitic plant with slender thread-like, yellow to orange vines that coil about and fasten to their host plants with wort-like attachments called haustoria. Dodder has several common names, among them tangle gut, love vine, strangle gut, devil's gut, witches shoelaces, gold thread, pull down, devil's ringlet, hellbind, hair weed, devil's hair and angel hair. The various species of dodder also have common names, among them field dodder (*Cuscuta campetris*), flax dodder (*C. epilinum*), clover dodder (*C. epithymum*), swamp dodder (*C. gronovii*), and largeseed dodder (*C. indicora*).

In the field, the dodder seeds will germinate and will initially be dependent upon the food stored within the seed. The dodder plant will die if it does not attach to a suitable host plant within several days after germination since it cannot produce the food necessary to sustain its growth. The stem of the dodder plant entwines itself about the host plant and penetrates the host plant by means of haustoria. Once a dodder plant has attached to the host plant, the part of the dodder stem between the point of attachment and the soil dies. The dodder plant is then totally dependent upon the host plant for its food, inorganic salts and water. Consequently, although typically not killed, the host plant has less food for its own growth, loses vigor and sustains physical damage from the penetration of the dodder. Once a crop field is infected, the dodder problem can be expected each year for many years as it is a very difficult pest to eradicate. Dodder is a widespread weed that attacks many crops of economic importance such as alfalfa, tomatoes, potatoes, cranberries, carrots, celery, broccoli and sugar beets.

A typical example of damage to a crop involves cranberries. Dodder generally attaches at a point below the cranberry flower bud which normally would develop into the following year's fruit. Because of the point of attachment, many buds die thus reducing the subsequent year's yield. More losses occur when the surviving cranberries become trapped in the network of dodder vines. Cranberries are usually water harvested. The cranberries are dislodged from the vines by paddles when the cranberry beds are flooded with water. The berries rise to the surface and are skimmed off. However, the network of dodder vines restrains many of the berries from rising to the surface thus preventing the complete harvesting of the crop. Because cranberries are a particularly lucrative cash crop, even the loss of one berry per square foot causes a significant financial drain on the farmer.

Because of the unique parasitic qualities of dodder and its disposition toward proliferation, dodder is a difficult plant to control. Prior art methods include flaming the dodder plant using, for example, propane weed burners; cutting the host plant below the point at which the dodder is attached and removing the dodder; spraying chemical herbicides on the dodder and completely burning the infested field to eradicate the dodder. However, these methods are not suitable for a variety of reasons. With respect to flaming, cutting the host plant, or burning the dodder, this results in the complete destruction of not only the dodder but also the host plant. Further, controlling dodder with chemical herbicides is difficult because herbicides are only effective against dodder when applied during a limited period of the plant's growth cycle prior to its attachment to the host plant. For a more detailed description of dodder and its prior art control, reference is made to the following two articles: *Cuscuta spp. (Dodder): A Literature Review of its Biology and Control*, Division of Agricultural Sciences, University of California, Bulletin 1880, August 1976; and Dawson, J. H. et al., *Dodder and Its Control*, prepared by Agricultural Research Service and Extension Service, United States Department of Agriculture, Farmer's Bulletin Number 2276, May 1984.

Certain plant pathogenic organisms are effective for controlling a variety of weeds in specific crops. The organisms may be exotic pathogens of the weed. Freeman, T. E. et al, 1976, "Status of the Use of Plant Pathogens in the Biological Control of Weeds," *Proc. IV Inter. Sym. Bio. Cntr. Wds.*, pp. 201–206. An exotic pathogen is defined as a disease-causing organism which is not indigenous to the site of the weed plant. An exotic pathogen of an identical or related species of indigenous weed may be imported for inoculation on the indigenous weed which evolved in the absence of the exotic pathogen and therefore has little or no genetic resistance to the exotic pathogen. Templeton, G. E., 1982, "Status of Weed Control with Plant Pathogens," In: *Biological Control of Weeds with Plant Pathogens*. R. Charudattan and H. L. Walker (eds.), John Wiley and Sons, New York, pp. 29–44.

Biological control agents may also be indigenous to the area. An example would be a mycoherbicide, an endemic fungus used as a biological herbicide for controlling native weed species. Mycoherbicides have been used in the past as biological controls. Walker reports the use of the fungus *Alternaria macrospora* as a biocontrol agent for spurred anoda (*Anoda cristata* (L.) Schlecht), a weed which infests and damages crops, especially cotton and soybean. Walker, H. Lynn, 1980, "*Alternaria macrospora* as a Potential Biocontrol Agent for Spurred Anoda: Production cf Spores for Field Inoculum," U.S. Dept. Agric., Sci. Ed. Admin., AAT-S-12. Additionally, research in the Soviet Union reports that dodder parasitizing alfalfa has been effectively controlled by using fungal spores of the *Alternaria* genus (Rudakov, O. L., 1963, "The First Results in the Biological Control of Cuscuta, Spp.", *Zashchita Rastenii Ot Vreditellwi Boleznei*, Moscow, 8:25–26) and species of *Alternaria* and *Fusaria* (Kovalev, O. V., 1971, "Modern Outlooks of Biological Control of Weed Plants in the U.S.S.R." Proc. II Inter. Sym. Bio. Cntr. Wds., p. 166.) However, neither the identification of the cultures of the *Alternaria* and *Fusarium* nor the methods of application were available. Additionally, the species of dodder controlled in these investigations were not adequately identified. Further investigations to try to obtain more information have proved unsuccessful. Consequently, many questions remain concerning the biological control of dodder.

SUMMARY OF THE INVENTION

The present invention is directed to the control of dodder utilizing specific mycoherbicides. The inventors have discovered a method for effectively controlling dodder without necessitating the use of harsh crop damaging procedures or chemical herbicides.

The present invention is accomplished by controlling the growth of dodder on field crops by introducing onto the dodder an effective amount of spores of a biologically pure endemic mycoherbicide selected from the group consisting of *Fusarium tricinctum*, a presently unidentified species of *Alternaria* and mutations thereof.

The inoculum which controls the dodder on field crops is also disclosed in this invention. As used here, the term "inoculum" means a biological control agent which is introduced onto a host substance. The inoculum comprises essentially biologically pure cultures of spores of the fungal species mentioned in the previous paragraph.

The mycoherbicides of the present invention represent a significant advance in controlling dodder. Because they are a biologically pure culture of a natural biological organism, massive quantities of the mycoherbicidal inoculum can be applied to dodder with little danger of environmental contamination. In view of public concern for groundwater contamination and aerial pollution from pesticides, mycoherbicidal control is an attractive alternative to chemical pesticides. Further, mycoherbicidal control is less expensive than control with conventional chemical herbicides.

Other objects, advantages and features of the present invention will become apparent from the following specification when taken in conjunction with the accompanying claims.

DETAILED DESCRIPTION OF THE INVENTION

The present invention discloses a method of biologically controlling dodder utilizing mycoherbicides. For a variety of probable reasons, the fungal control agents of the present invention have not effectively controlled dodder in agricultural crops. Chief among these reasons were ground cultivation and antifungal (herbicidal) measures commonly undertaken in the cultivation of crop plants which effectively reduced the presence of both harmful and beneficial fungi thus indirectly encouraging the success of dodder. It was found that by inoculating dodder infested fields with the mycoherbicides under circumstances that allow the fungi to infect and damage the dodder, dodder could be successfully controlled.

Specifically, it has been discovered here that swamp dodder (*Cuscuta gronovii* Willd.) and *Cuscuta compacta* Juss. can be effectively controlled by one or more of the following fungi used separately or in combination: *Fusarium tricinctum*, an unidentified species of *Alternaria*, also referred to herein as Alternaria sp., and mutations of these. These beneficial fungi and their spores will sometimes hereinafter be referred to as the "beneficial" or the "mycoherbicidal" fungi and spores or simply as "mycoherbicides." To identify mycoherbicidal strains of these fungi and enable others to obtain a culture of these fungal inoculants, a sample of an effective strain of *Fusarium tricinctum* has been deposited with the American Type Culture Collection (ATCC) on Jan. 28, 1987, receiving Accession Number 20832, and a sample of the unidentified species of *Alternaria* has been deposited with the ATCC on Jan. 28, 1987, receiving Accession Number 20831.

The spores of the beneficial fungi may be mass produced in culture with relative ease. The spores are cultured in a suitable culture medium such as modified Richard's medium (Walker, H. Lynn, supra.) as a substrate until mycelia are produced. Mycelia are a tangled mass of hyphal filaments which make up the vegetative body or thallus of a fungus, similar to the mat of mold that grows on bread. Once mycelia are produced, they are taken from the media and placed in shallow pans under conditions of light and high humidity to effect spore production. After spore production is observed, the mycelia are removed from the humidity and allowed to mature. As the mycelia mature, essentially biologically pure cultures of the spores are formed that may be vacuumed off the mycelia and collected in biologically pure culture. The term "biologically pure culture" is used herein to mean cultures of spores which have essentially no concentration of spores of other fungal species sufficient to interfere with the controlling infection of dodder exposed thereto. A "controlling infection" is defined below. The spores can then be used to infect the dodder plant.

The mycoherbicidal spores are then preferably combined with a biologically non-interfering liquid carrier for spray application onto the dodder plant. A carrier shall be deemed "biologically non-interfering" if it does not prevent the infection of dodder by mycoherbicidal spores carried thereby when the spores so carried are applied to the dodder. The preferred carrier is a water-base liquid, preferably distilled water, containing a minor amount, not more than 5% v/v and preferably about 0.05% v/v, of a non-ionic surfactant. The non-ionic surfactant may be any of a number of widely used non-ionic surface active substances known to the art for use in reducing the surface tension of the liquid carrier. The concentration of the spores in the liquid carrier is preferably approximately $5 \times 10^5$ spores per milliliter carrier although a higher or lower concentration may be utilized as desired. In any event, an effective concentration, defined as a concentration sufficient to cause a controlling infection of dodder when applied thereto, must be used. The particular concentration may vary with application rate and the like. An infection of dodder shall be deemed a "controlling infection" if the dodder so infected is reduced in its robustness, its seed production capacity, its ability to invade or continue to invade the crop plant infested by the dodder or any combination of such signs of control.

Although a liquid carrier is preferred, any carrier that provides a convenient means for distributing spores over dodder to be controlled falls within the scope and spirit of the invention. Dusts, for example, are among such carriers well known to those skilled in the art.

Recited below are examples of the practice of the present invention. It is to be understood that the present invention is defined by the claims contained herein and that these examples are for illustrative purposes only.

EXAMPLE 1

The following example was designed to test certain fungi for effectiveness in infecting dodder. Isolates of two fungi were obtained from diseased dodder tissue found in an uncultivated marsh. The diseased tissue was surfaced sterilized by immersion in a 0.5% v/v solution of sodium hypochlorite (Clorox-Reg. TM) for 30 seconds, followed by a 30 second rinse in sterile distilled water. The tissue was then placed on three types of media: (1) a standard potato dextrose agar (PDA), (2) PDA with 100 parts per million (ppm) of the antibiotic novobiocin added, and (3) a standard water agar (WA). Pure cultures of an Alternaria species and a Fusarium species were obtained.

Cultures of both the Alternaria and the Fusarium were grown on PDA and placed under fluorescent lights with a 12 hour photoperiod until they sporulated. The Alternaria culture was identified as belonging to this genus by the typical muriform conidia which were wider at the base than at the apex. Under high magnification much of the observed proliferation constituting a single aerial clump were identified as false beaks or rostra, also called secondary conidiophores. The spores were actually erostrate and relatively small, similar to those of *Alternaria alternata*. But the prevalence of prominent secondary conidiophores is more nearly characteristic of a group of species that are known to be the asexual stage of of the ascomycete genus Lewia Barr & Simmons. The isolate may be an as yet undisclosed species, but at present a species name cannot be assigned. The isolate is, however, most likely a species from the *Alternaria conjuncta/Alternaria infectoria* complex. The color of the aerial mycelium and conidia was dark brown. Cultures of Fusarium were identified as belonging to this genus by the typical fusiform macroconidia, and the presence of both microconidia and chlamydospores. The particular *Fusarium* was identified as *Fusarium tricinctum* based on the lunate shape of the macroconidia, which are divided into four cells. The basal cell is plainly pedicellate, and the two end cells are of equal size and are approximately equidistant from the widest portion of the conidium. The microconidia are single celled and are typically napiform, citriform and pyriform shaped. In addition, the sclerotia formed in culture were cream colored and the mycelium was a deep wine red, characteristic of *F. tricinctum*.

The culture, grown according to the procedure described above, was induced to sporulate and the spores were used to infect swamp dodder (*C. gronovii* Willd.) growing on carrots in a controlled environment as follows. Carrots were grown in 6 inch plastic pots. The environmental conditions were as follows:

| | |
|---|---|
| Radiation: | 760 micro-einstein/m²/sec |
| Photoperiod: | 16 hours |
| Relative Humidity: | 70% day and night |
| Automatic Watering: | 3.5 minutes every 6 hours utilizing half strength Hoagland's Solution* |
| Temperature: | 25° C. day, 20° C. night |
| Lights On and Off: | Gradually - 0.5 hour at 20%, 0.5 hour at 50%, then 100% |

When the carrots were in the four leaf stage, dodder seedlings which had been germinated in a 30° C. growth chamber were placed in contact with the carrot foliage. The host-parasite system was allowed to grow for two weeks after parasitism had occurred. At this time plants were inoculated with spores from one of the fungi.

The spores were obtained by growing cultures of the fungi in petri plates. The Alternaria was cultured on PDA and the *F. tricinctum* on a hay agar. The cultures were induced to sporulate by placing them under cool white fluorescent lights with a 12 hour photoperiod. The spores were washed from the surface using sterile distilled water, and the concentration determined using a hemacytometer. The concentration of the solution was adjusted to $5\times10^5$ spores per milliliter. Water with 0.05% v/v Tween 20 (Reg. TM), a non-ionic surfactant, was used as a carrier. The spore suspensions were applied with an atomizer. The plants were sprayed individually with 20 ml of the spore suspension. Both carrot and dodder tissue were wetted. Control plants (uninoculated controls) were sprayed with sterile distilled water containing the surfactant.

After the suspension had dried on the foliage, a mist system was used to provide surface moisture. The mist system was automatically timed to turn on for 25 seconds every 2.5 minutes for 3 days following inoculation. Lesions developed on the dodder host that were identical to the symptoms seen in field sites.

The isolates obtained were then cultured as before and induced to sporulate. The spores were characterized and identified as *Fusarium tricinctum* and Alternaria sp. as initially isolated, thus confirming Koch's Postulates. Agrios, George N., 1970, *Plant Pathology*. Academic Press Inc., New York, p. 14. The spores were suspended as previously stated and applied to dodder in the same manner as before. An analysis of the data obtained by inoculating swamp dodder with reisolated *F. tricinctum* is presented in Table 1 below, and an analysis of the data obtained by inoculating swamp dodder with reisolated Alternaria sp. is presented in Table 2 below.

TABLE 1

| | Inoculated with *F. tricinctum* | Uninoculated Controls | Total Plants |
|---|---|---|---|
| plants with no symptoms* | 1 | 28 | 29 |
| plants with symptoms | 39 | 5 | 44 |
| total plants | 40 | 33 | 73 |
| % plants with symptoms | 98 | 15 | 60 |

TABLE 2

| | Inoculated with Alternaria sp. | Uninoculated Controls | Total Plants |
|---|---|---|---|
| plants with no symptoms* | 1 | 28 | 29 |
| plants with symptoms | 48 | 5 | 53 |
| total plants | 49 | 33 | 82 |
| % plants with symptoms | 98 | 15 | 65 |

*Symptoms appeared as small, oval dark brown lesions.

The results illustrated above in Tables 1 and 2 show that these fungi are fungal pathogens of swamp dodder.

EXAMPLE 2

Example 2 describes a field test designed to test the post-emergent treatment of dodder. A cranberry field in which dodder was present and well developed (post-emergent dodder) was sprayed with a mixture of Alternaria and Fusarium spores mixed in a carrier of water and a surfactant as follows.

Spores of both Alternaria sp. and *Fusarium tricinctum* were raised on hay agar and used to inoculate 500 ml cultures of modified Richard's medium. One culture of each fungus was placed on a mechanical shaker at 21°

C. and shaken at 110 revolutions per minute for 3 days. The cultures were then filtered through a nylon screen to separate the mycelia from the medium. The mycelia were poured into shallow plastic pans lined with aluminum foil. These were then placed in plastic bags with a wet sponge in order to maintain a near saturation environment. The cultures were placed under sodium halide lamps which had a high intensity of 71 to 81 einstein/$m^2$/sec as measured with a LI-COR LI 185 (Reg. TM) photometer. The photoperiod was controlled with automatic timers to provide 6 hours daylight, 15 hours dark, 12 hours daylight, 15 hours dark. After sporulation, the spores were removed from the surface of the cultures with a cyclone spore trap. Tervet, I.W. et al., 1950, "A Simple Device for Collection of Fungus Spores," *Plant Disease Reporter* 34(8), p. 238. The spores which were collected from each fungus were stored separately at 4° C.

After 2 weeks the spores of each species were collected, combined and were applied to swamp dodder which was actively growing in a cranberry marsh. The spores were resuspended in distilled water so that the concentration of each species was $5\times10^5$ spores per milliliter. A non-ionic surfactant (Tween 20-Reg. TM) was added at 0.05% v/v. The suspension was applied to plots which were 1 meter wide and 3 meters long arranged in a randomized complete block with 4 replications. A $CO_2$ back pack sprayer delivering 380 liters/hectare at 25 psi through 8003 flat fan nozzles, known to the art, spaced 53 centimeters apart and held 46 centimeters above the plants was used. After a ten day incubation, the plants were visually rated for percent control of swamp dodder. The dodder displayed disease symptoms, and samples of the dodder were collected and *Fusarium tricinctum* and Alternaria sp. identical to original isolates were cultured from lesions on dodder plants from the field to determine the cause of the symptoms. Two additional ratings were made at one week intervals. An untreated control was included in the test at a distance which insured that there would be no contamination from the treatment.

Ten days after spraying, about 62.5% of the dodder had been destroyed. By 24 days after spraying, over 90% of the dodder had been destroyed. Thus, it is clear that the fungal inoculants applied to the dodder provided an effective control for the dodder.

EXAMPLE 3

Cranberries, carrots, celery, mint, alfalfa, and potatoes each were tested with Alternaria sp. ATCC 20831 and *Fusarium tricinctum* ATCC 20832 to verify that none of them were attacked by either of the fungi. With each crop plant, 15 plants were exposed to an effective concentration of 1 of the 2 fungi. Another 15 plants were exposed to the other fungus, and a third group of plants were exposed to neither fungus. The plants were kept under the humidity, mist, temperature, and light conditions described in Example 1. Any lesions appearing on the plants were examined for fungal strains, and all fungal isolates taken from such lesions were compared with the fungi to which the plants had been exposed.

None of the plants of any of the crop plants notes above were found to have been infected by either of the fungi. The close similarity of tomatoes, egg plant, and peppers to potatoes allows one skilled in the art to predict like results with those plants. Red clover was observed in the field to be unaffected by the two fungi, which were infecting dodder that was in the immediate vicinity of the clover. The diverse nature of these plants and the other crop plants tested establishes that either fungus may be used to control dodder on a wide variety of crop plants.

The control of dodder with a mycoherbicide is advantageous for several reasons. First, the host plant does not appear to be adversely affected by the application of the mycoherbicide. Second, the mycoherbicide provides an effective means for controlling dodder without the necessity for chemical herbicides. Third, the permanency, environmental safety and economy of biological control as opposed to chemical control provides strong inducements toward the utilization of mycoherbicides for controlling dodder.

Although not required, it may be feasible to coordinate application of fungal and chemical herbicides in a sequential manner for controlling dodder on crop plants without harming the crop plants. The fungal application normally follows the chemical herbicide application.

We claim:

1. A method of controlling the growth of dodder on field crops comprising the step of introducing onto the dodder an effective amount of spores of the mycoherbicide *Fusarium tricinctum* and mutations thereof.

2. The method according to claim 1 wherein the dodder is swamp dodder (*Cuscuta gronovii* Willd.).

3. The method according to claim 1 wherein the *Fusarium tricinctum* is of the strain ATCC Accession Number 20832.

4. The method according to claim 1 wherein the spores are diluted in a carrier to no less then an effective concentration.

5. The method according to claim 4 wherein the spores are applied to the dodder at a rate not less than $5\times10^5$ spores per milliliter.

6. The method according to claim 1 wherein the control of the dodder is accomplished by means of the spores of mycoherbicides in combination with a chemical herbicide applied in sequential manner wherein said spore application follows said chemical herbicide application.

7. A biological inoculum for controlling the growth of dodder on field crops comprising an essentially biologically pure culture of spores of the mycoherbicide *Fusarium tricinctum* and mutations thereof.

8. The biological inoculum of claim 7 wherein the *Fusarium tricinctum* is of the strain ATCC Accession Number 20832.

9. The biological inoculum according to claim 7 wherein the spores are diluted to not less than an effective concentration in a biologically non-interfering carrier.

* * * * *